Figure 1:
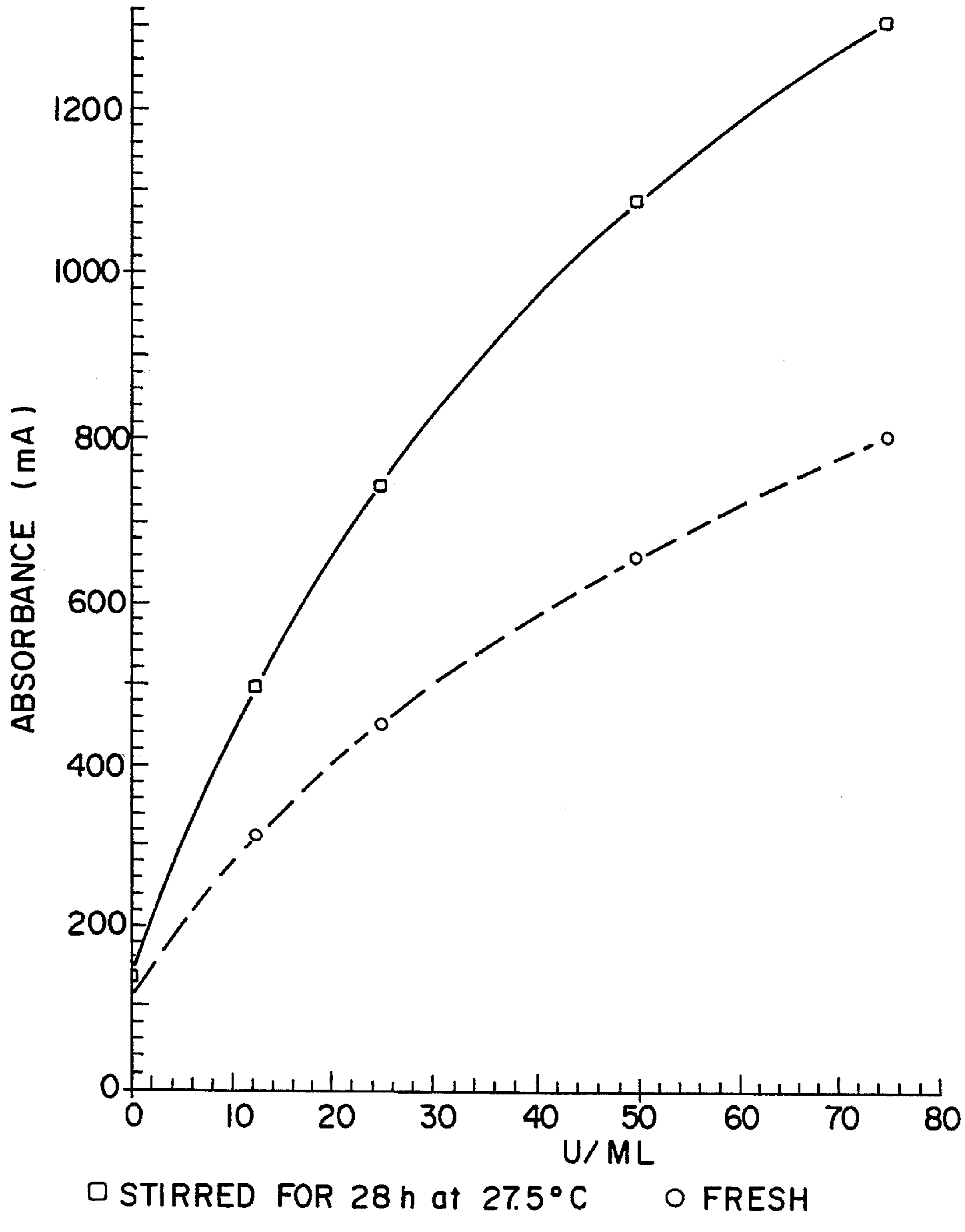

US005459033A

United States Patent [19]

Vonwirth et al.

[11] Patent Number: 5,459,033

[45] Date of Patent: Oct. 17, 1995

[54] VIRUS SOLUTION FOR USE IN IMMUNOASSAYS

[75] Inventors: Heiner Vonwirth, Heiningen; Michael Marschall, Munich; Hubert Bayer, Weilheim, all of Germany

[73] Assignee: Boehringer Mannheim GmbH, Mannheim, Germany

[21] Appl. No.: 41,979

[22] Filed: Apr. 2, 1993

[30] Foreign Application Priority Data

Apr. 3, 1992 [DE] Germany .......................... 42 11 108.0

[51] Int. Cl.[6] .................................................. G01N 33/576

[52] U.S. Cl. .......................... 435/5; 435/235.1; 435/962; 436/820; 436/826

[58] Field of Search ............................... 435/5, 962, 236, 435/238, 239, 235; 424/89, 93 T; 436/826, 820

[56] References Cited

U.S. PATENT DOCUMENTS

| | | | |
|---|---|---|---|
| 4,291,019 | 9/1981 | Lupton et al. | 435/236 |
| 4,471,054 | 9/1984 | Lattore et al. | 435/238 |
| 4,588,680 | 5/1986 | Bucher et al. | 435/5 |
| 4,695,537 | 9/1987 | Dorsett | 435/5 |
| 4,790,987 | 12/1988 | Compans et al. | 530/388.3 |
| 4,808,518 | 2/1989 | Dorsett et al. | 435/5 |

FOREIGN PATENT DOCUMENTS

| | | | |
|---|---|---|---|
| 37931 | 10/1981 | European Pat. Off. . | |
| 0173295 | 3/1986 | European Pat. Off. . | |
| 0226182A1 | 6/1987 | European Pat. Off. . | |
| 278487 | 8/1988 | European Pat. Off. . | |
| 0351248 | 1/1990 | European Pat. Off. . | |
| 0379216A1 | 7/1990 | European Pat. Off. . | |
| 0402757A3 | 12/1990 | European Pat. Off. . | |
| 0473065A2 | 3/1992 | European Pat. Off. . | |
| 3907651 | 1/1990 | Germany . | |
| 8187862 | 11/1983 | Japan | 435/962 |
| WO90/04182 | 4/1990 | WIPO . | |

OTHER PUBLICATIONS

M. Khristova et al., Acta Virol., vol. 33, No. (1), pp. 1–7 (1989).

H. Willkommen et al., Acta Virol., vol. 27, No. (5), pp. 407–411 (1983).

*Primary Examiner*—Mary E. Ceperley
*Attorney, Agent, or Firm*—Nikaido, Marmelstein, Murray & Oram

[57] ABSTRACT

The invention concerns a virus solution which contains a detergent having the general formula I and serves to stabilize the virus solution as well as its production and use in heterogeneous immunoassays for the detection of antibodies against viruses.

20 Claims, 1 Drawing Sheet

VIRUS SOLUTION FOR USE IN IMMUNOASSAYS

The present invention concerns a virus solution which contains a detergent having the general formula I

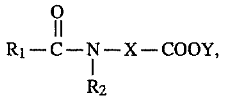

(I)

in which

R1: is a hydrophobic residue,

R2: is H or an alkyl residue with 1–6 C atoms,

X: is an alkyl residue with 1–6 C atoms and

Y: is an alkaline or an alkaline earth ion, as well as its production and use in a heterogeneous immunoassay for the detection of antibodies against viruses.

Antibodies are often determined in viral diagnostics in order to detect an infection. Antibodies of the IgM sub-class are formed during the early phase of an infection and they persist for several months. They are therefore suitable for monitoring the acute progress of the disease. Neutralizing antibodies, usually of the IgG sub-type, occur at a very early stage in the course of the disease and persist for many years. Their detection is of particular value for studies of epidemics and for evaluating vaccine protection.

Immunological methods are being increasingly used for the detection of antibodies. A multitude of variants is known and in this connection competitive, immunoradiometric and immunoenzymometric assays as well as sandwich assays are known. Various variants are listed for example in an article by A. H. W. M. Schuurs and B. H. van Weemen in "Dt. Ges. f. klin. Chemie e.V.—Mitteilungen 1/1979". Among these a test procedure is described in which an antibody is bound to a solid phase and this antibody is directed against the antibody subclass from which the antibody to be determined is derived from. The sample solution which contains the antibody to be determined is incubated in the presence of this solid phase with its specific antigen and with a labelled antibody which is also capable of binding to the antigen. In this process the antibody to be determined and the added labelled antibody compete for binding to the antigen. The immunocomplexes are immobilized by the antibody bound to the solid phase and detected.

If in this test variant the antigen has several epitopes and thus enables the simultaneous binding of the antibodies to be determined and the labelled antibodies without these two antibodies competing with one another or there being only a weak competition, then a detectable complex can form from the antibody bound to the solid phase, the antibody to be determined, the antigen and the labelled antibody.

Depending on the choice of labelled antibody and antigen, the antibody to be determined is thus detected by an indirect (competitive binding method) or by a direct method.

In a further variant of the test an antibody against the viral antigen is bound to the solid phase. The sample solution which contains the antibody to be determined is incubated with the antibody's specific viral antigen and with a labelled antibody which is also capable of binding to the viral antigen. In this process the antibody which is bound to the solid phase, the labelled antibody and the antibody to be determined compete for binding to the antigen.

The antibody which is bound to the solid phase does not have to be bound directly to the solid phase but can, if desired, be bound via a pair which specifically bind to one another as disclosed in DE-A 3907651. A conjugate of a specifically bindable receptor and a substance S which is a partner of a pair which specifically bind to one another, is then used as the antibody. The other partner of the binding pair which specifically bind to one another is coupled to the solid phase.

In all test variants a viral antigen is added for the detection of the virus-specific antibody. This viral antigen consists of viral particles or parts thereof.

These viruses or viral components are commercially available in the form of lyophilisates or concentrated solutions which have to be diluted to a ready-to-use concentration immediately before use. As a contribution towards an improved and easier handling endeavours are being made to offer solutions which are ready for use and already diluted. However, diluted virus solutions are very often not sufficiently stable on storage and cause large variations in the measurement signal which cannot be tolerated. The exact cause of the instability is not known. It is possible that some viruses, especially viral particles, which have hydrophobic components tend to form aggregates. A further disadvantage of this aggregate formation is that the measurement signal is lowered by this. In order to achieve a sufficiently sensitive measurement larger amounts of viruses have to be added to the test to compensate for this.

This phenomenon is particularly pronounced in viruses which cause hepatitis, in particular hepatitis A viruses as well as herpes viruses. .

The object of the present invention was therefore to avoid the disadvantages of the state of the art and in particular to find a way of stabilizing viruses, especially those which tend to form aggregates, in a ready-to-use solution and to avoid variations in the measurement signal by this means. At the same time when this virus solution is used in immunoassays, the sensitivity should be as high as possible.

This object is achieved by the invention which is characterized in the claims. This object is in particular achieved by a solution containing viruses or particles thereof to which a detergent is added having the general formula I,

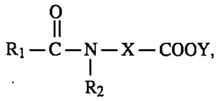

(I)

in which

R1: is a hydrophobic residue,

R2: is H or an alkyl residue with 1–6 C atoms,

X: is an alkyl residue with 1–6 C atoms and

Y: is an alkaline or alkaline earth ion.

The present invention in addition concerns a process for stabilizing virus solutions, the production of the virus solution as well as its use in a heterogeneous immunoassay for the determination of antibodies against viruses.

The invention further concerns an improved method for the determination of antibodies against viruses based on a heterogeneous immunoassay by incubating the sample with the solution according to the present invention and at least two receptors R1 and R2, of which R1 mediates binding to the solid phase and is capable of specific binding to the antibody to be determined or to the viruses present in the solution and R2 is a conjugate of a receptor which is capable of specific binding to viruses present in the solution and a label, separating the complex which forms from the solution and measuring the label in one of the phases.

Surprisingly, it is possible to stabilize the ready-to-use solution by use of the detergent of the general formula I. At the same time the measurement signal increases when using the same amount of viral material and by this means the sensitivity of the test is increased. The increase in sensitivity of the test can also be achieved by other ionic detergents. However, a long-term stability of the ready-to-use virus solution is not observed in any case except when the detergent according to the invention having the general formula I is added. With the other detergents which were tested an initial increase in the signal was observed in the test. When the ready-to-use virus solution is stored, usually at 4° C., a significant uncontrollable decrease in signal occurs which can lead to inaccurate measurement results.

The detergents which can be used in the virus solution according to the present invention are anionic detergents having the general formula I

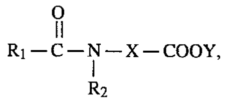

(I)

R1 denotes a hydrophobic residue and usually represents a straight-chain or branched-chain alkyl residue with 6–20 C atoms. R2 and X denote straight-chain or branched-chain alkyl residues with 1–6 C atoms. Y denotes a cation. All cations can be used which do not lead to insolubility of the compound. These are in particular alkaline or alkaline earth ions, preferably sodium or potassium.

The sodium salt of N-lauroyl sarcosine (SLS) having the general formula II is particularly preferred.

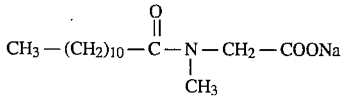

(II)

In order to produce the virus solution the detergent of formula I is added to a purified virus standard and is diluted to the ready-to-use concentration. The concentration of the detergent in the ready-to-use solution is 0.01–1% by weight, preferably 0.04–0.4 and particularly preferably 0.08–0.12 % by weight. In addition to the detergent and the viral particles or parts thereof, the solution can also contain the usual test additives such as for example buffer, albumin or preservatives.

Those viruses which are distinguished by a strong tendency to aggregate are especially used as viruses. These are in particular viruses which cause hepatitis such as hepatitis A, B, C, D and E viruses as well as herpes viruses. Exellent results were obtained using the hepatitis A viruses (HAV). Apart from complete viral particles, parts thereof such as the virus membrane, the capsid or capsid proteins can also be present in the solution. The concentration of the viruses or viral components is selected so that the solution can be used directly i.e. an additional dilution is not necessary before use. Thus the concentration is adjusted according to the requirements of the respective detection method.

The solution containing viruses is incubated after adding the detergent. Depending on the employed incubation temperature of 2°–35° C., stabilization is achieved after about 15 hours to 10 days. Incubation for 26–30 hours at 25°–30° C. has proven to be particularly suitable. After this incubation period the ready-to-use virus solution remains stable for a period of several months when stored at 4° C.

The virus solution according to the present invention is used in heterogeneous immunoassays for the determination of antibodies against viruses.

The present invention therefore also concerns such heterogeneous immunoassays for the determination of antibodies against viruses in which the virus solution according to the present invention is used as an essential component. In the method for the determination of antibodies against viruses according to the present invention based on the heterogeneous immunoassay technique, the sample is incubated with the virus solution which is stable on storage and with at least two further receptors R1 and R2. Receptor R1 mediates binding to the solid phase. Depending on whether class-specific or subclass-specific antibodies such as IgM, $IgG_1$, $IgG_2$ or IgA or the complete antibody content of the sample is to be determined, receptor R1 is capable of specific binding to the antibody to be determined or to the viruses present in the solution which is stable on storage.

A conjugate consisting of a receptor which is capable of specific binding to the antibody to be determined or to the viruses present in the solution which is stable on storage and a specifically bindable substance S can also be used as receptor R1. The specifically bindable substance S of receptor R1 mediates binding to the solid phase. In this case the specifically bindable substance S is preferably a partner of a binding pair which specifically bind to one another. Such pairs are known to a person skilled in the art. The following pairs are suitable: antigen-antibody; hapten-antibody; biotin-avidin/streptavidin; protein-antiprotein; protein A-immunoglobulin; haemoglobin-haptoglobin or enzyme-substrate. A hapten such as for example digoxin, p-nitrophenol, saponin, FITC and in particular biotin is preferably used as S. Binding of S to the receptor capable of specific binding to the antibody to be determined or to the viruses present in the solution according to the present invention is carried out in a known way. Methods are known to a person skilled in the art.

The second receptor R2 employed, is a conjugate of a receptor which is capable of specific binding to the viruses present in the solution according to the present invention and a label. An enzyme, a radioactive substance, an isotope, a fluorescent or chemiluminescent substance can be used as the label, the determination of which is carried out according to one of the methods familiar to a person skilled in the art. The conjugate is produced according to well-known methods.

A receptor R1 which is capable of specific binding to the antibody to be determined is used to detect class-specific or subclass-specific antibodies against the virus present in the stable solution. Immunoglobulin class-specific or subclass-specific monoclonal or polyclonal antibodies come into consideration as receptor R1. An antibody or antibody fragment is used as the receptor which is capable of specific binding in conjugate R2. Depending on whether or not this antibody recognizes the same epitope on the viruses as the antibody to be determined and whether one or several identical epitopes are present on the viruses, receptor R2 competes with the antibody to be determined for binding to the viral antigen or binds simultaneously to the viral antigen. In the preferred test variant in which the sample antibodies and receptor R2 either do not compete or only to a slight extent, a complex of receptor R1 bound to the wall, sample antibody, viral antigen and receptor R2 forms after incubation of the test components. Increasing concentrations of sample antibody result in an increasing measurement signal.

In the test for the total content of antibody in the sample, a receptor R1 is used which is capable of specific binding to the viral antigen in the same way as receptor R2. The receptors capable of specific binding used in this case as receptors R1 and R2 are antibodies or fragments thereof which are capable of binding to the viruses present in the solution according to the present invention. Since these receptors capable of specific binding are to compete with the antibody to be determined for binding to the virus, it is essential that receptors are used in this case whose reaction with the virus is similar to that of the antibody to be determined, i.e. they have a similar binding capacity. Therefore one alternative is to use polyclonal antibodies for each of the receptors R1 and R2 having the same binding capacity as the antibody to be determined. It is also possible to use monoclonal antibodies if it can be ensured that the epitopes on the viral antigen recognized by these monoclonal antibodies are also recognized by the antibody to be determined. In this test variant an increasing concentration of antibody in the sample produces a decreasing measurement signal.

In both test variants immobilization of the complex which forms to the solid phase is mediated by receptor R1 which is either bound directly to the solid phase or can be bound to the solid phase via the substance S. In the latter variant, the partners of the specifically bindable pair which are complementary to S are bound to the solid phase in a known manner. Polymer materials, materials containing cellulose or glass are suitable as the solid phase. Polystyrene, polymethacrylate, Teflon, polyamide, copolymers of styrene and acrylnitrile, glass and cellulose products have proven to be particularly suitable. The solid phase can be present in any desired form, for example as tubes, microtritre plates, beads, film, powder, particles or a fibre fleece.

The component capable of specific binding can be bound to the solid phase in a well-known manner. This binding to the solid phase can be carried out either directly or via a spacer or binding protein. For example the method described in the Patent Application DE-A-3640412 for the production of a solid phase matrix is a suitable method.

In the detection of class-specific and subclass-specific antibodies using the preferred test variant in which sample antibody and receptor R2 both simultaneously bind to the virus and thus finally a complex of receptor R1, sample antibody, virus and receptor R2 forms, the first step in the test procedure is to incubate receptor R1, which is either bound directly to the solid phase or is preferably bound to the solid phase via substance S with the sample in the reaction vessel.

A complex of receptor R1 and sample antibody which is bound to a solid phase is formed first. In a second step which can be preceded by a washing step if necessary, the virus solution according to the present invention is added and it is incubated again. In a third step in the procedure receptor R2 which carries the label is added by pipette. If necessary a washing step can also be included between the second and third step.

After incubating again the solid phase is separated from the liquid phase and the label is determined in a fourth step of the procedure in one of the two phases.

Receptor R2 is present as a concentrate and has to be diluted before use to the desired concentration with a suitable buffer which can contain further common additives such as stabilizers of the label or preservatives.

It has proven to be particularly preferable to dilute receptor R2 before use with the solution according to the present invention which contains the viruses instead of with a special buffer. The solution according to the present invention can in this case contain further additives which for example serve to stabilize receptor R2. In this solution a complex of receptor R2 and virus forms. This preformed immunocomplex can be used directly after the first incubation step in which receptor R1 and sample antibody are incubated.

In the third step in the procedure the label is then determined directly. This simplifies and accelerates the test procedure which previously required four working steps.

Furthermore the present invention concerns a test kit for the determination of antibodies which contains the receptors R1 and R2, the virus solution which is stable on storage as well as the solid phase whereby R1 is capable of specific binding to the antibody to be determined or to the viruses present in the solution which is stable on storage and is bound directly to the solid phase or is a conjugate of a receptor which is capable of specific binding to the antibody to be determined or to the viruses present in the solution which is stable on storage and a substance S which is capable of specific binding and R2 is a conjugate of a receptor which is capable of specific binding to the viruses present in the solution which is stable on storage and a label.

Either a solid phase to which receptor R1 is bound or, as a preferred form, a solid phase to which a component is bound which is capable of specific binding to S is used as the solid phase. The immobilization is preferably carried out via the specific binding pair biotin-avidin/streptavidin.

Receptors R1 and R2 and the solution according to the present invention are present physically separated from one another in the test kit. Receptor R1 can be directly coupled to the solid phase. If receptor R1 is a conjugate of S and a receptor which is capable of specific binding and furthermore a component which is capable of specific binding to S is bound to the solid phase, then the solid phase is present physically separated from receptors R1, R2 and the solution according to the present invention.

It is intended to elucidate the invention by the following figures and examples:

EXAMPLE 1

Production of a hepatitis A virus solution (HAV solution) which is stable on storage The hepatitis A virus starting material was obtained from the Mediagnost Company, FR Germany. The solution which is stable on storage has the following composition:

40 mM sodium phosphate buffer pH 7.4

50 mM di-sodium tartrate 0.1% N-lauroylsarcosine, sodium salt 0.1% preservative 0.2% bovine serum albumin hepatitis A virus The content of hepatitis A virus differs from batch to batch and is adjusted on the basis of the signal i.e. so that approximately the same signal is obtained in the immunological test.

The solution is stirred for 28 hours at 27.5° C. after addition of the HAV antigen.

EXAMPLE 2

Anti-HAV IgM test

The solution prepared in this way was used in the commercially available Enzymun-Test® Anti-HAV-IgM from the Boehringer Mannheim GmbH Company. The following solutions were used:

Solution 1 (Incubation buffer)

40 mM phosphate buffer pH 7.0 ca. 1.5 μg/ml biotinylated anti-human IgM monoclonal mouse antibody

Solution 2 anti-HAV monoclonal mouse antibody,

POD labelled ca. 1 U/ml POD

Negative control: human serum, which is negative for anti-HAV

Positive control: human anti-HAV IgM in human serum

Solution 2 was mixed with the HAV solution which had been stored for different periods of time in a ratio of 100:1 (HAV solution: solution 2) and incubated for at least one hour before the test procedure.

In a first step 10 μl sample (negative control or positive control) was incubated for 90 minutes at 25° C. with 500 μl incubation buffer in polystyrene tubes coated with streptavidin. During this the biotinylated anti-human IgM antibody binds to the IgM present in the sample and also to the tube wall coated with streptavidin.

After washing once, 500 μl of the mixture of HAV solution and solution 2 is added to the tube by pipette in a second step and incubated for 90 minutes at 25° C. In this second step the preformed detection complex of HAV antigen and anti-HAV antibody-POD conjugate in the mixture of HAV solution and solution 2 specifically binds to the anti-HAV IgM of the sample that is bound to the wall.

After a further washing step, 500 μl substrate chromogen solution (100 mM phosphate/citrate buffer pH 4.4 containing 3.2 mM sodium perborate is mixed with an equal portion of 1.9 mM ABTS® at least one hour before carrying out the test) is added to the tube by pipette and the colour formed is determined photometrically at 405 nm after a 60 minute incubation at 25° C.

EXAMPLE 3

Comparison of the signal level between freshly prepared HAV solution and the HAV solution according to the present invention The HAV solution prepared according to example 1 was used with a freshly prepared HAV solution in the anti-HAV IgM test according to example 2 and the same buffer composition was used. The results are shown graphically in FIG. 1. A significant increase in the signal level (ca. 1.6-fold) was achieved using the HAV solution according to the present invention in comparison with the freshly prepared HAV solution. Thus the sensitivity of the test is increased when using the same amount of HAV material. If the sensitivity of the test was not critical then the amount used in the test can be reduced by using the HAV solution according to the present invention which is particularly advantageous in the case of the expensive HAV raw material.

EXAMPLE 4

Long-term stability of the HAV solution

The HAV solution prepared according to example 1 was stored at 4° C. and subsequently the signal level which could be attained using this solution was determined in the anti-HAV test according to example 2. The values are shown in Table 1. As proven by control experiments, the observed slow drift towards slightly lower signals is due to the liquid POD conjugate (solution 2) that had to be used as well and likewise stored at 4° C. for the periods indicated in the table.

TABLE 1

Storage stability of the HAV solution

| Storage period at 4° C. (months) | Absorbance (mA) at 405 nm: negative control | Absorbance (mA) at 405 nm: positive control |
|---|---|---|
| 0 | 150 | 1015 |
| 1 | 142 | 1036 |
| 2 | 136 | 1120 |
| 3 | 141 | 989 |
| 4 | 125 | 922 |
| 5 | 147 | 907 |
| 6 | 128 | 872 |
| 9 | 132 | 785 |

EXAMPLE 5

Influence of the incubation temperature during production

The HAV solution was prepared as described in example 1 with the difference that the solution was incubated for different periods at various temperatures after addition of the HAV antigen. Subsequently the signal level was determined in the anti-HAV IgM test according to example 2 using a positive control as sample. The measured absorbances are shown in Table 2. The absorbance is increased in all cases from ca. 400 mA to ca. 1000 mA. At low temperatures of 4° C. this process takes ca. 7 days. On the other hand, at 25 and 30° C. an approximately one day incubation is sufficient. After this incubation period the HAV solutions prepared in this way are stable on storage i.e. the signal level no longer decreases to the initial value during storage and remains, as shown in the previous example, constant over a longer period.

TABLE 2

Influence of the incubation temperature during production

| Production temperature | Absorbance (mA) of the positive control at the times stated: 3h | 1d | 2d | 3d | 4d | 7d | 10d |
|---|---|---|---|---|---|---|---|
| 4° C. | 371 | 553 | 645 | 780 | 853 | 1004 | 979 |
| 13° C. | 402 | 608 | 792 | 921 | 1065 | 1035 | 1067 |
| 18° C. | 418 | 712 | 931 | 990 | 1101 | 1037 | 1044 |
| 25° C. | 440 | 957 | 1022 | 1051 | 1098 | 1074 | 1049 |
| 30° C. | 475 | 982 | 1071 | 1104 | 1098 | 1107 | 1059 |

We claim:

1. A solution for immunoassays, containing Hepatitis A viruses and parts thereof and an amount of detergent sufficient to stabilize the virus against aggregate formation having the general formula I

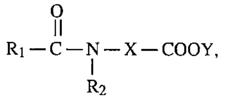

(I)

in which $R_1$ is a hydrophobic residue, $R_2$ is H or a $C_1$–$C_6$ alkyl,

X is a $C_1$–$C_6$ alkyl, and

Y is an alkali metal or an alkaline earth metal ion, produced by adding to a solution containing said viruses and parts thereof said detergent I and incubating the mixture for 18 hours to 10 days at 2°–35° C.

2. Solution of claim 1 wherein said solution further contains a labelled receptor R2 which is capable of specific binding to the viruses or parts thereof.

3. The solution of claim 1 wherein the detergent is N-lauroyl sarcosine.

4. The solution of claim 1, wherein the mixture is incubated for 26–30 hours at 25°–30°C.

5. A method for the determination of antibodies against Hepatitis A viruses wherein said method comprises:

1) incubating a sample which may contain antibodies against the virus with the solution of claim 1 and additionally at least two receptors R1 and R2 to form a complex if antibodies are present, wherein R1 mediates binding to the solid phase and is capable of specific binding to the viruses present in the solution, and R2 is a conjugate of a) a receptor capable of specific binding to the viruses present in the solution and b) a label, 2) separating the complex which forms from the solution, and 3) measuring the label in one of the phases wherein the measurement of the label is an indication of the presence or amount of the antibodies to be determined.

6. A method for the determination of antibodies of a certain immunoglobulin class or subclass against Hepatitis A viruses by a heterogenous immunoassay wherein said method comprises:

1) incubating a sample which may contain antibodies against the virus with the solution as claimed in claim 2 and at least one receptor R1 which mediates binding to the solid phase and is capable of specific binding to the antibody to be determined to form a complex if antibodies are present, 2) separating the complex which forms from the solution, and 3) measuring the label in one of the phases wherein the measurement of the label is an indication of the presence or amount of the antibodies to be determined.

7. The method of claim 6, wherein the steps are done in the following order:

1) a sample which may contain antibodies against the virus is incubated with the receptor R1, 2) the solution is added after an optional washing step, 3) separating the complex which forms from the solution, and 4) the label is measured in one of the phases wherein the measurement of the label is an indication of the presence or amount of the antibodies to be determined.

8. The method of claim 5 wherein a conjugate of a receptor which is capable of specific binding to the viruses present in the solution and a substance S is used as receptor R1, wherein S is a partner of a binding pair which specifically bind to one another, and a solid phase is used to which components are bound which are capable of specific binding to S.

9. The method of claim 6 wherein a conjugate of a receptor which is capable of specific binding to the antibody to be determined and a substance S is used as receptor R1, wherein S is a partner of a binding pair which specifically bind to one another, and a solid phase is used to which components are bound which are capable of specific binding to S.

10. A method of stabilizing Hepatitis A viruses and parts thereof in a solution for immunoassays, said method comprising adding an amount of detergent sufficient to stabilize the virus against aggregate formation having the general formula I

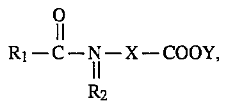
(I)

to a solution of said viruses and parts thereof wherein $R_1$ is a hydrophobic residue, $R_2$ is H or a $C_1$–$C_6$ alkyl, X is a $C_1$–$C_6$ alkyl, and Y is an alkali metal or an alkaline earth metal ion and incubating the mixture for 18 hours to 10 days at 2°–35° C.

11. A method of stabilizing Hepatitis A viruses and parts thereof in a ready-to-use diluted solution for immunoassays, said method comprising adding an amount of detergent sufficient to stabilize the virus against aggregate formation having the general formula I

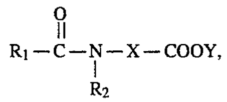
(I)

to a solution of said viruses and parts thereof wherein $R_1$ is a hydrophobic residue, $R_2$ is H or a $C_1$–$C_6$ alkyl, X is a $C_1$–$C_6$ alkyl, and Y is an alkali metal or an alkaline earth metal ion and incubating the mixture for 18 hours to 10 days at 2°–35° C.

12. The method of claim 10 wherein the detergent is N-lauroyl sarcosine.

13. The method of claim 11 wherein the concentration of the detergent is 0.01–1% by weight.

14. A test kit for the heterogeneous immunoassay determination of antibodies, wherein said kit contains, separately packaged, the solution of claim 1, the receptors R1 and R2, a solid phase, whereby R1 mediates binding to the solid phase and is capable of specific binding to the viruses present in the solution, and

R2 is a conjugate of a receptor which is capable of specific binding to the viruses present in the solution and a label.

15. A test kit of claim 14, wherein said kit contains receptor R1 as a conjugate of a receptor capable of specific binding to the viruses present in the solution and a substance S, wherein S is a partner of a binding pair which specifically bind to one another and is capable of specific binding to the solid phase.

16. A test kit of claim 15, wherein said kit contains receptor R1 with biotin as the substance S capable of specific binding to the solid phase, and a solid phase on the surface of which avidin or streptavidin is bound.

17. A method for the determination of antibodies against Hepatitis A viruses wherein said method comprises:

1) incubating a sample which may contain antibodies against the virus with the solution of claim 1 and additionally at least two receptors R1 and R2 to form a complex consisting of R1, the antibodies to be determined, the virus and R2 if antibodies are present in the sample, wherein R1 mediates binding to the solid phase and is capable of specific binding to the antibody to be determined, and R2 is a conjugate of a) a receptor capable of specific binding to the viruses present in the solution and b) a label, 2) separating the complex from the solution, and 3) measuring the label in one of the phases wherein the measurement of the label is an indication of the presence or amount of the antibodies to be determined.

18. The method of claim 17, wherein a conjugate of a receptor which is capable of specific binding to the antibody to be determined and a substance S is used as receptor R1, wherein S is a partner of a binding pair which specifically bind to one another, and a solid phase is used to which components are bound which are capable of specific binding to S.

19. A test kit for the heterogeneous immunoassay determination of antibodies, wherein said kit contains, separately packaged, the solution of claim 1, the receptors R1 and R2, a solid phase, whereby R1 mediates binding to the solid phase and is capable of specific binding to the antibody to be determined, and R2 is a conjugate of a receptor which is capable of specific binding to the viruses present in the solution and a label.

20. A test kit of claim 19, wherein said kit contains receptor R1 as a conjugate of a receptor capable of specific binding to the antibody to be determined and a substance S, wherein S is a partner of a binding pair which specifically bind to one another and is capable of specific binding to the solid phase.

* * * * *